US008844365B2

(12) United States Patent
Gregg et al.

(10) Patent No.: US 8,844,365 B2
(45) Date of Patent: Sep. 30, 2014

(54) MEASURING BIOLOGICAL TISSUE

(71) Applicant: Boston Scientific Scimed, Inc., Maple Grove, MN (US)

(72) Inventors: Peter W. Gregg, Santa Cruz, CA (US); Devin Bridgen, Durham, NC (US); Daniel Hildebrand, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/889,795

(22) Filed: May 8, 2013

(65) Prior Publication Data
US 2013/0302845 A1  Nov. 14, 2013

Related U.S. Application Data

(60) Provisional application No. 61/644,273, filed on May 8, 2012.

(51) Int. Cl.
*G01B 7/16* (2006.01)
*G01N 33/483* (2006.01)

(52) U.S. Cl.
CPC ................................ G01N 33/4833 (2013.01)
USPC .............................................. 73/779; 73/856

(58) Field of Classification Search
CPC . G01N 3/20; G01N 2203/0023; A61B 8/485; G01L 1/2206
USPC ................... 73/826, 849, 818, 856–860, 779
See application file for complete search history.

(56) References Cited

U.S. PATENT DOCUMENTS

| | | | | |
|---|---|---|---|---|
| 3,934,450 A | * | 1/1976 | Reed | 72/383 |
| 4,589,288 A | * | 5/1986 | Porter et al. | 73/852 |
| 5,178,017 A | * | 1/1993 | Dinzburg | 73/849 |
| 5,892,157 A | * | 4/1999 | Syre | 73/812 |
| 5,983,729 A | * | 11/1999 | Taylor | 73/849 |
| 6,245,105 B1 | | 6/2001 | Nguyen et al. | |
| 6,413,275 B1 | | 7/2002 | Nguyen et al. | |
| 7,096,743 B2 | * | 8/2006 | Vogel et al. | 73/849 |
| 7,516,644 B2 | * | 4/2009 | Wong et al. | 73/12.07 |
| 7,546,775 B2 | * | 6/2009 | Chinavare | 73/849 |
| 7,690,265 B2 | * | 4/2010 | Cipra | 73/851 |

\* cited by examiner

*Primary Examiner* — Max Noori
(74) *Attorney, Agent, or Firm* — Fish & Richardson P.C.

(57) ABSTRACT

A tissue measurement system includes a clamp, a measuring head, and a deflection sensor. The clamp includes a first plate and a second plate releasably engageable with one another to secure a substantially planar biological tissue. In the engaged position, the first and second plates define at least a portion of a test section along which a portion of the secured substantially planar biological tissue is disposed. The measuring head is movable toward the test section and into contact with the portion of the substantially planar biological tissue disposed along the test section. The deflection sensor is responsive to movement of the biological tissue contacted by the measuring head.

18 Claims, 12 Drawing Sheets

MEASURING BIOLOGICAL TISSUE

CROSS-REFERENCE TO RELATED APPLICATION

This application claims priority under 35 USC §119(e) to U.S. Provisional Patent Application Ser. No. 61/644,273, filed on May 8, 2012, the entire contents of which is hereby incorporated by reference.

TECHNICAL FIELD

The following disclosure relates to measuring biological tissue and, more particularly, to measuring one or more stress characteristics of biological tissue for implantation in a mammal.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft).

Biological tissue can have mechanical properties that vary within a single donor and/or from among several donors of the same species. For example, biological tissue from a single donor can have non-uniform thickness and/or stiffness, and the average thickness and/or stiffness of biological tissue can vary from one donor to another. The variation in mechanical properties of biological tissue used in replacement heart valves can impact the performance and/or durability of a replacement heart valve implanted in a patient.

SUMMARY

Tissue measurement determines one or more mechanical properties of biological tissue used for implantation in a mammal.

In one aspect, a tissue measurement system includes a clamp, a measuring head, and a deflection sensor. The clamp includes a first plate and a second plate releasably engageable with one another (e.g., with a force of between about 0.5 lbf to about 5 lbf) to secure therebetween a substantially planar biological tissue. The first and second plates, in an engaged position, define at least a portion of a test section along which a portion of the secured substantially planar biological tissue is disposed. The measuring head is movable relative to the test section and into contact with the portion of the substantially planar biological tissue disposed along the test section. The deflection sensor is responsive to movement of the biological tissue contacted by the measuring head.

In some embodiments, the tissue measurement system further includes a receptacle coupled to the measuring head such that a load supported in the receptacle is transmittable to the biological tissue disposed along the test section.

In certain embodiments, the measuring head includes a substantially rounded surface movable into contact with the biological tissue to apply a point load perpendicular to the biological tissue disposed along the test section. Additionally or alternatively, the measuring head includes a substantially rounded elongate surface movable into contact with the biological tissue to apply an axial load perpendicular to the biological tissue disposed along the test section.

In some embodiments, the first plate includes a first magnetic portion and the second plate includes a second magnetic portion. The polarities of the first and second magnetic portions can be oriented to attract one another for releasable engagement of the first and second plates of the clamp. Additionally or alternatively, with the first and second plates in the engaged position, the first magnetic portion and the second magnetic portion can be aligned along an axis extending in a direction perpendicular to the substantially planar biological tissue secured between the first and second plates in the engaged position. In certain embodiments, the first magnetic portion includes a first magnet embedded in the first plate and the second magnetic portion includes a second magnet embedded in the second plate. For example, a first potting material can secure the first magnet in the first plate, and a second potting material can secure the second magnet in the second plate. Each of the first and second magnets can be made of one or more of samarium-cobalt, aluminum-nickel-cobalt, and ceramic. The first and second plate can be one or more of stainless steel and plastic.

In certain embodiments, the tissue measurement system further includes a plurality of needles, the first plate includes a first plurality of orifices, and the second plate includes a second plurality of orifices. Each of the plurality of needles can be positionable in one of the first plurality of orifices and one of the second plurality of orifices to releasably engage the first plate to the second plate.

In some embodiments, the measuring head is movable into a contact with a first surface of the biological tissue and the deflection sensor is responsive to movement of a second surface of the biological tissue opposite the first side of the biological tissue. For example, the deflection sensor can include a spring-loaded spindle movable in a first direction to contact the second side of the biological tissue and movable in a second, opposite direction in response to movement of the second side of the biological tissue.

In certain embodiments, the test section has an area less than a surface area of the secured substantially planar biological tissue. For example, the test section can have a cross-sectional area about equal to the surface area of a native heart leaflet and/or a cross-sectional area less than or equal to about 1.0 in$^2$. Additionally or alternatively, the test section can extend through the clamp and have a substantially uniform cross-sectional area (e.g., having a substantially rectangular cross-sectional area) in a direction through the clamp. In certain embodiments, the ratio of the surface area of the substantially planar biological tissue secured between the first and second plates to the cross-sectional area of the test section in a direction through the clamp is about 1.5:1 to about 4:1. In some embodiments, each of the first and second plates has a respective substantially planar surface and the first section and the second plates are releasably engageable with one another to secure the substantially planar biological tissue between the respective substantially planar surfaces.

In certain embodiments, the test section extends through the first and second plates and is entirely defined by the first and second plates in the engaged position.

In some embodiments, each of the first and second plates includes a respective gasket (e.g., a gasket made of silicone) and the first and second plates are releasably engageable with one another to secure the substantially planar biological tissue between the respective gaskets.

In certain embodiments, the measuring head is positionable at any point along the cross-sectional area of the test section.

In some embodiments, the deflection sensor is in electrical communication with a computer, and the deflection sensor is configured to send to the computer a signal representative of displacement.

In another aspect, a tissue measurement system includes a first clamp, a second clamp, a measuring head, and a deflection sensor. The first clamp includes a first plate and a second plate, the first and second plates releasably engageable with one another to secure therebetween a substantially planar biological tissue. The first and second plates, in an engaged position, defining at least a first portion of a test section along which a portion of the secured substantially planar biological tissue is disposed. The second clamp including a third plate and a fourth plate, the third and fourth plates releasably engageable with one another to secure therebetween the substantially planar biological tissue. The third and fourth plates, in an engaged position, defining at least a second portion of a test section along which a portion of the secured substantially planar biological tissue is disposed. The measuring head movable toward the test section and into contact with the portion of the substantially planar biological tissue disposed along the test section. The deflection sensor is responsive to movement of the biological tissue contacted by the measuring head.

In some embodiments, the first portion of the test section defined by the engaged first and second plates is substantially coplanar and perpendicular to the second portion of the test section defined by the engaged third and fourth plates.

In certain embodiments, the first and second clamps are separately removable from the substantially planar biological tissue.

In some embodiments, the measuring head includes a substantially rounded elongate surface movable into contact with the biological tissue to apply an axial load perpendicular to the biological tissue disposed along the test section. Additionally or alternatively, the measuring head can be movable to apply the axial load along one or more axes intersecting the first clamp and/or the second clamp.

In still another aspect, a method of measuring tissue includes placing a substantially planar biological tissue, releasably engaging a second plate to a first plate such that the substantially planar biological tissue is secured between the first and second plates, applying a load to the substantially planar biological tissue, and measuring deflection of the substantially planar biological tissue. The substantially planar biological tissue is placed on a planar surface at least partially formed by the first plate. The first and second plates define at least a portion of a test section along which a portion of the secured substantially planar biological tissue is disposed. The load is applied to the portion of the substantially planar biological tissue disposed along the test section. The measured deflection of the substantially planar biological tissue is in response to the applied load.

In some embodiments, applying the load includes placing a weight into a receptacle in communication with a measuring head movable perpendicular to and into contact with the substantially planar biological tissue disposed along the test section. Additionally or alternatively, applying the load includes applying a dynamic load to the substantially planar biological tissue disposed along the test section. In certain embodiments, applying the load includes moving a measuring head into contact with the substantially planar biological tissue disposed along the test section to apply a point load and/or an axial load perpendicular to the biological tissue disposed along the test section.

In certain embodiments, the method of measuring tissue further includes positioning the first plate in an orifice defined by a frame. The first plate and the frame form the planar surface. Additionally or alternatively, releasably engaging the second plate to the first plate includes placing the second plate on the substantially planar biological tissue disposed on the planar surface. In certain embodiments, releasably engaging the second plate to the first plate includes aligning respective magnetic portions of the first and second plates.

In some embodiments, the method of measuring tissue further includes comparing the measured deflection to a selection range.

In certain embodiments, the method of measuring tissue further includes cutting a leaflet from the substantially planar biological tissue disposed along the test section. Cutting the leaflet can be based at least in part on the comparison of the measured deflection to the selection range.

In some embodiments, the method of measuring tissue further includes repositioning the first and second plates along the substantially planar biological tissue. For example, repositioning the first and second plates along the substantially planar biological tissue can be based at least in part on the comparison of the measured deflection to the selection range. Additionally or alternatively, repositioning the first and second plates can include detaching the first and second plates from one another and moving the first and second plates relative to the substantially planar biological tissue.

In certain embodiments, the method of measuring tissue further includes measuring thickness of the substantially planar biological tissue disposed along the test section.

In some embodiments, the method of measuring tissue further includes releasably engaging a third plate to a fourth plate such that the substantially planar biological tissue is secured between the third and fourth plates. The third and fourth plates can define at least a portion of the test section coplanar to and perpendicular to the portion of the test section defined by the first and second plates. In certain embodiments, applying the load to the portion of the substantially planar biological tissue includes applying an axial load along one or more axes intersecting a first clamp comprising the first and second plates and/or intersecting a second clamp comprising the third and fourth plates.

Embodiments can include one or more of the following advantages.

In some embodiments, a first and a second plate are releasably engageable to secure a biological tissue therebetween and define at least a portion of a test section. Such releasable engagement of the first and second plates can facilitate analysis of the biological tissue to identify portions of the biological tissue exhibiting one or more desirable mechanical properties (e.g., stress-strain relationships, thickness, etc.) for use in a replacement heart valve. For example, such releasable engagement can be achieved rapidly, while providing a stable platform for the application of force to the biological tissue. Additionally or alternatively, as compared to a "droop test" in which deflection of biological tissue is observed under the force of gravity, such releasable engagement of biological tissue can facilitate applying a range of loads to the biological tissue (e.g., to match the magnitude and position of physiological loads).

In certain embodiments, the first and the second plate are releasably engageable through magnetic force between magnetic portions of the first and second plates. As compared to securing biological tissue by piercing or otherwise physically deforming the biological tissue, such magnetic attraction between the plates can facilitate analysis of a portion of a large piece of biological tissue without damage to the biological tissue. For example, the first and second plates can be repeatedly detached and attached along multiple, different portions of the biological tissue without damaging the biological tissue. This can allow multiple, different small portions of a large piece of biological tissue to be analyzed before one or more of the small portions of the biological tissue is selected and cut for use as a leaflet in a replacement heart valve. This can improve the yield associated with a single large piece of biological tissue.

In some embodiments, a first and a second clamp define at least a portion of a test section along which a portion of substantially planar biological tissue is disposed. The first clamp and the second clamp can be separately removed from the biological tissue to facilitate application of force along one or more axes parallel to the biological tissue. For example, the first and second clamps can be separately removed from the biological tissue to facilitate measuring the response to the application of biaxial stress on the biological tissue disposed along the test section. The measurement of deflection in response to the biaxial stress can facilitate selection of biological tissue that will match mechanical performance of native leaflets under normal physiological operation. Additionally or alternatively, the measurement of deflection in response to the biaxial stress can facilitate matching portions of biological tissue to form matching leaflets.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
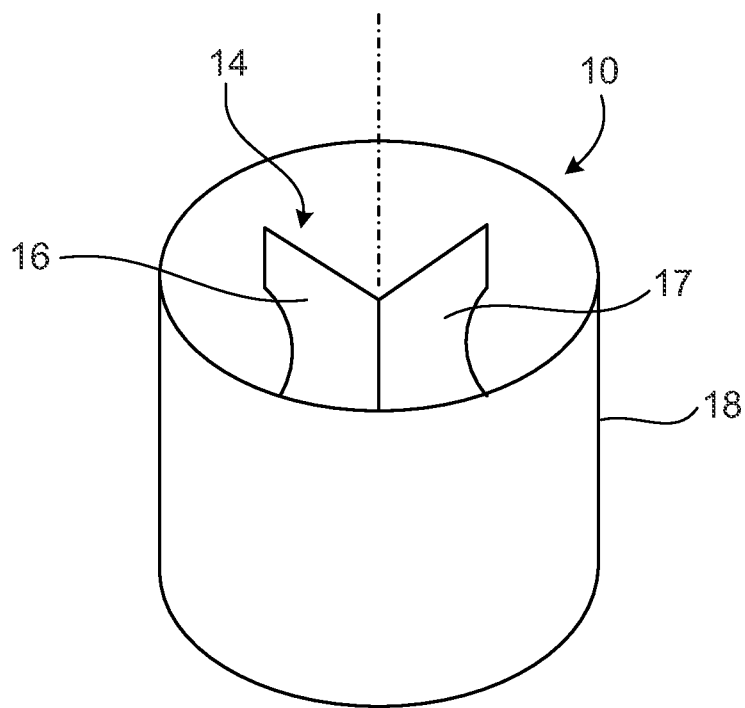
FIG. 1 is a perspective view of a prosthetic heart valve.
Figure 2:
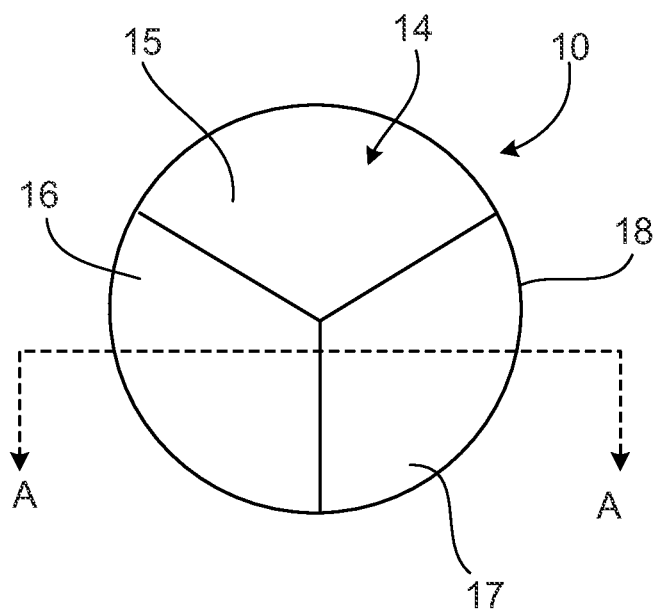
FIG. 2 is a top view of the prosthetic heart valve of FIG. 1.
Figure 3:
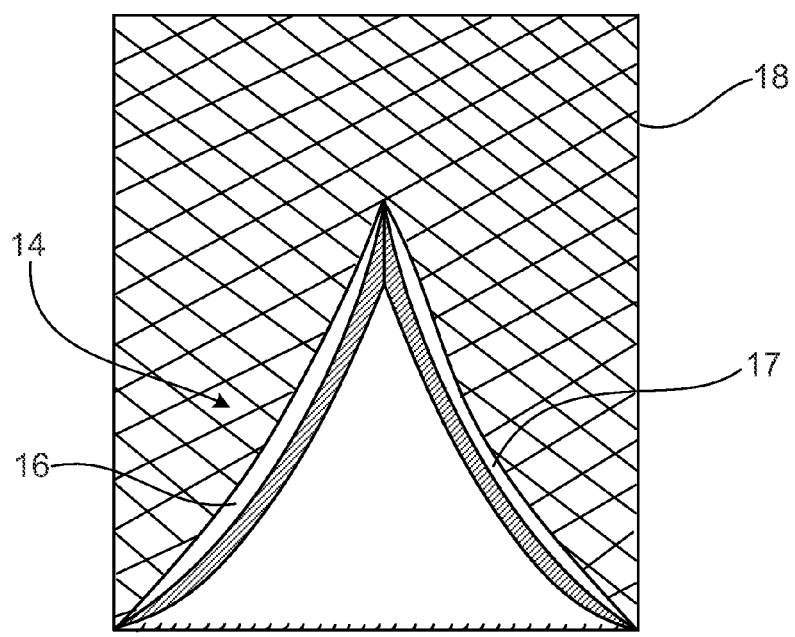
FIG. 3 is a cross-sectional view of the prosthetic heart valve of FIG. 1 along cross-section A-A.

Referring to FIGS. 1-3, a replacement heart valve 10 can be percutaneously delivered to an implantation site (e.g., an aortic heart valve) and/or surgically implanted at the implantation site to replace the function of a native mammalian heart valve. The replacement heart valve 10 includes a leaflet assembly 14 mounted on a stent 18, with the leaflet assembly 14 including leaflets 15, 16, 17 at least partially formed of biological tissue.

During use, the leaflets 15, 16, 17 move in and out of engagement with one another to regulate the flow of blood through the replacement heart valve 10 in a manner analogous to the physiological function of the native heart valve being replaced. For example, at least a portion of the leaflets 15, 16, 17 are movable away from one another to allow blood to flow through the replacement heart valve 10 in a first direction, and at least a portion of the leaflets 15, 16, 17 are movable into coaptation with one another (shown in FIG. 3) to limit the flow of blood through the replacement heart valve 10 in a second direction substantially opposite the first direction.

Figure 4:
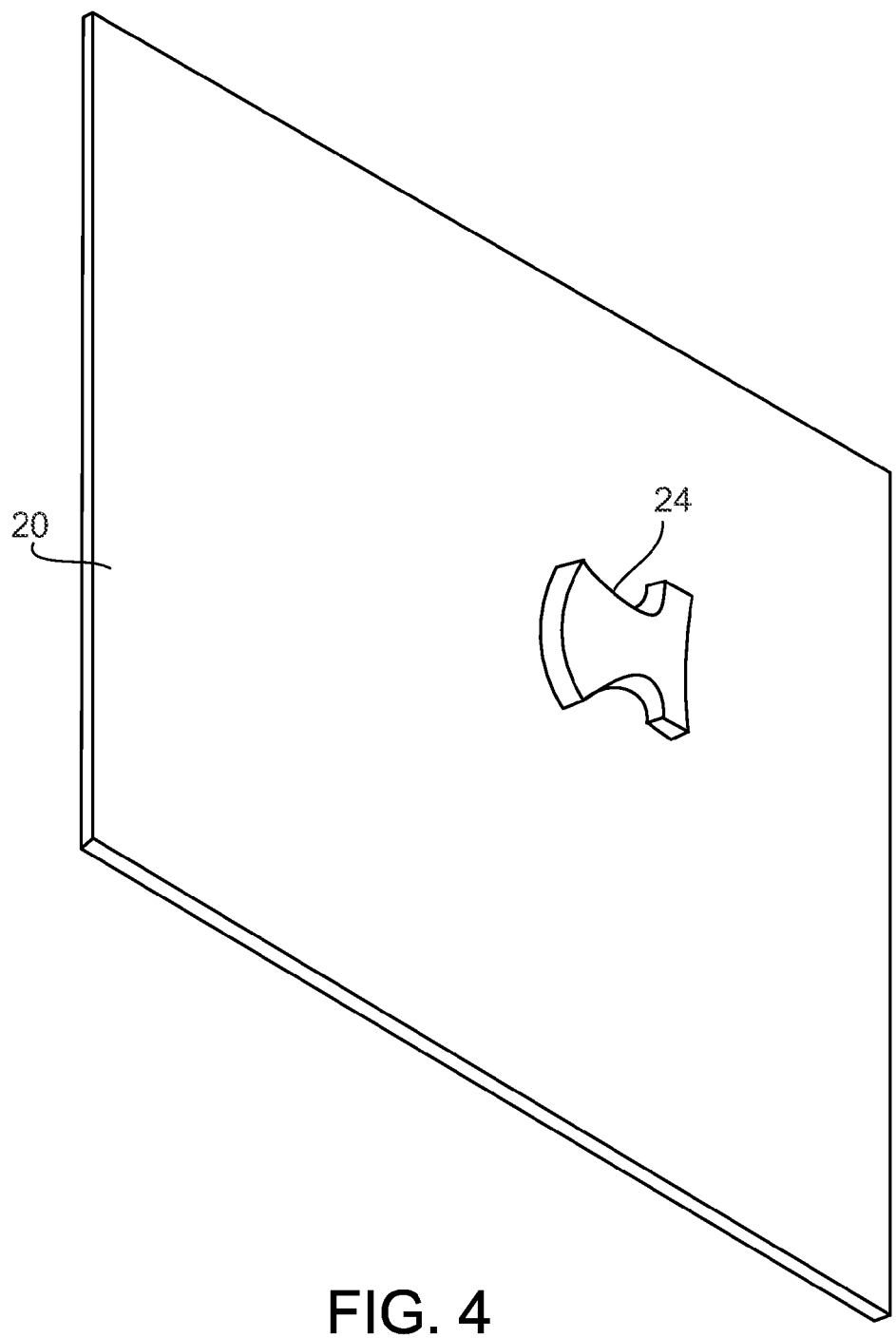
FIG. 4 is a schematic representation of a biological tissue and cutting die.

Referring now to FIG. 4, each of the leaflets 15, 16, 17 is formed by cutting or otherwise separating the leaflet 15, 16, 17 from a larger piece of a substantially planar biological tissue 20 (e.g., bovine pericardium, porcine pericardium, and/or equine pericardium). For example, in the embodiment shown in FIG. 4, a die 24 is positioned over a desired portion of the biological tissue 20 and then pressed onto the biological tissue 20 to form one or more of the leaflets 15, 16, 17. It should be appreciated that the leaflets 15, 16, 17 may be formed from different areas of the same piece of biological tissue or from different pieces of biological tissue.

The leaflets 15, 16, 17 are formed from biological tissue having substantially matching mechanical properties. Given the inherent variability of mechanical properties of biological tissue, each of the leaflets 15, 16, 17 are selected from portions of one or more pieces of planar biological tissue 20 such that one or more mechanical properties of the leaflets 15, 16, 17 are substantially similar. Such matching of the mechanical properties of the leaflets 15, 16, 17, the leaflets 15, 16, 17 can be coupled to one another to substantially match the hemodynamic characteristics of normal native leaflets. Additionally or alternatively, matching of the mechanical properties of the leaflets 15, 16, 17 can improve endurance of the replacement heart valve 10 by reducing, for example, the likelihood that the leaflets 15, 16, 17 will wear unevenly over time.

In some embodiments, each of the leaflets 15, 16, 17 can be formed from biological tissue exhibiting a stress-strain relationship (e.g., over a physiological range of stresses) that matches the corresponding stress-strain relationship of one or more of the other leaflets and falls within an acceptable range. Unless otherwise specified, the stress-strain relationship referred to herein is the portion of the stress-strain curve corresponding to elastic deformation of the biological tissue 20 such that the loads applied to the biological tissue 20 do not substantially change the mechanical properties of the biological tissue 20.

As described in further detail below, the stress-strain relationship of the substantially planar biological tissue 20 can be measured at various points along the substantially planar biological tissue. One or more of the leaflets 15, 16, 17 can be removed from portions of the substantially planar biological tissue 20 having a stress-strain response within an acceptable range. As also described in further detail below, the stress applied to the biological tissue 20 can be applied as a point load on the biological tissue 20. Additionally or alternatively, the stress applied to the biological tissue can be applied as an axial load on the biological tissue 20. For example, the stress applied to the biological tissue can be applied as a load perpendicular to the biological tissue 20 disposed along the test section 29 and along an axis parallel to the biological tissue 20 disposed along the test section 29. Such axial loading can improve the accuracy of stress matching of the portions of the biological tissue 20 selected for the leaflets 15, 16, 17.

Matching of the mechanical properties of the leaflets 15, 16, 17 before the leaflets are cut from the substantially planar biological tissue 20 can improve the yield associated with cutting leaflets from a piece of biological tissue such that less biological tissue is wasted during the process of making the leaflet assembly 14 of the replacement heart valve 10. Additionally or alternatively, such matching of the mechanical properties of the leaflets 15, 16, 17 before the leaflets are cut from the substantially planar biological tissue can improve the uniformity of mechanical properties of the leaflets 15, 16, 17 forming a given replacement heart valve 10.

Figure 5:
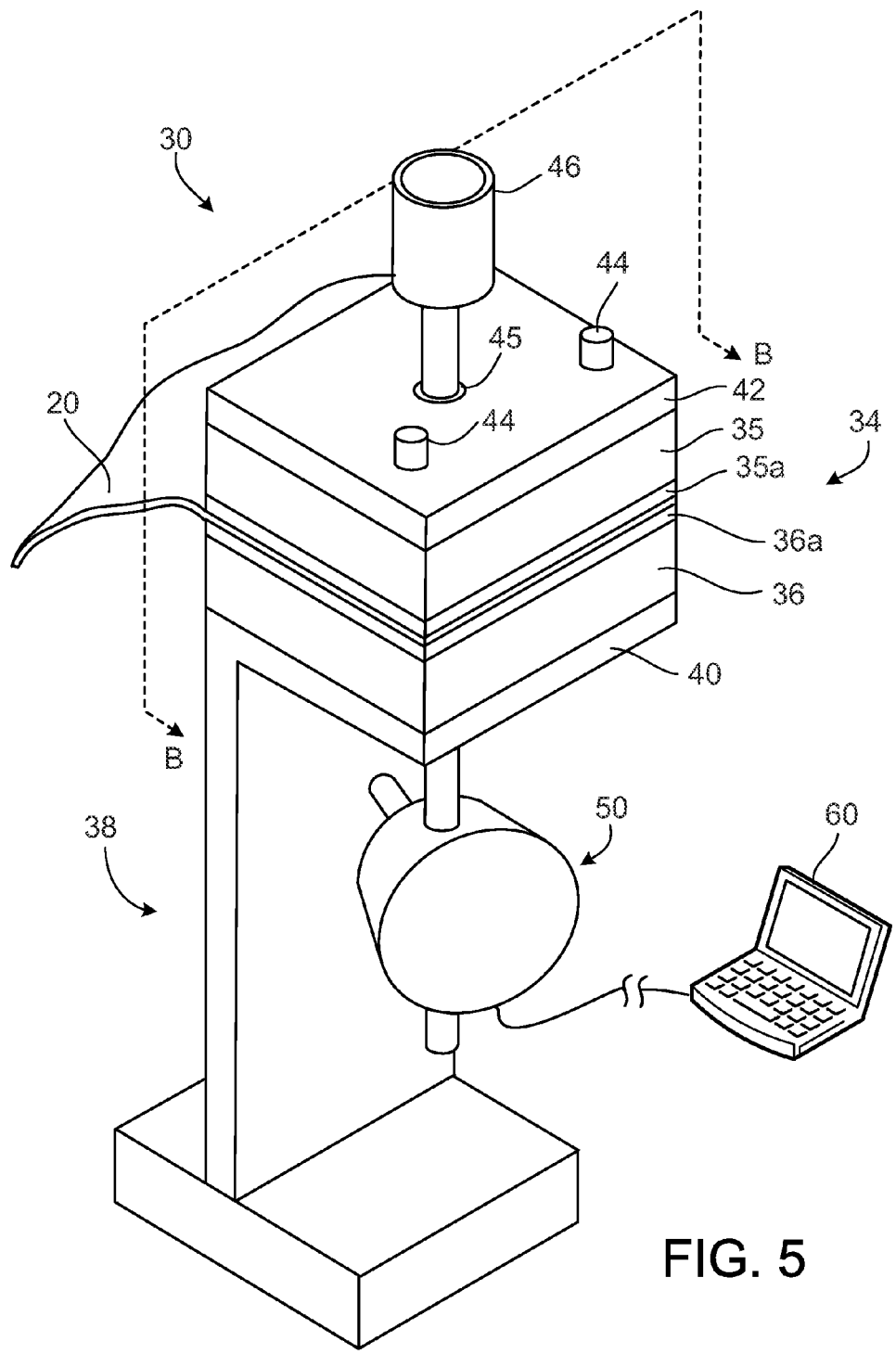
FIG. 5 is a perspective view of a tissue measuring system.
Figure 6:
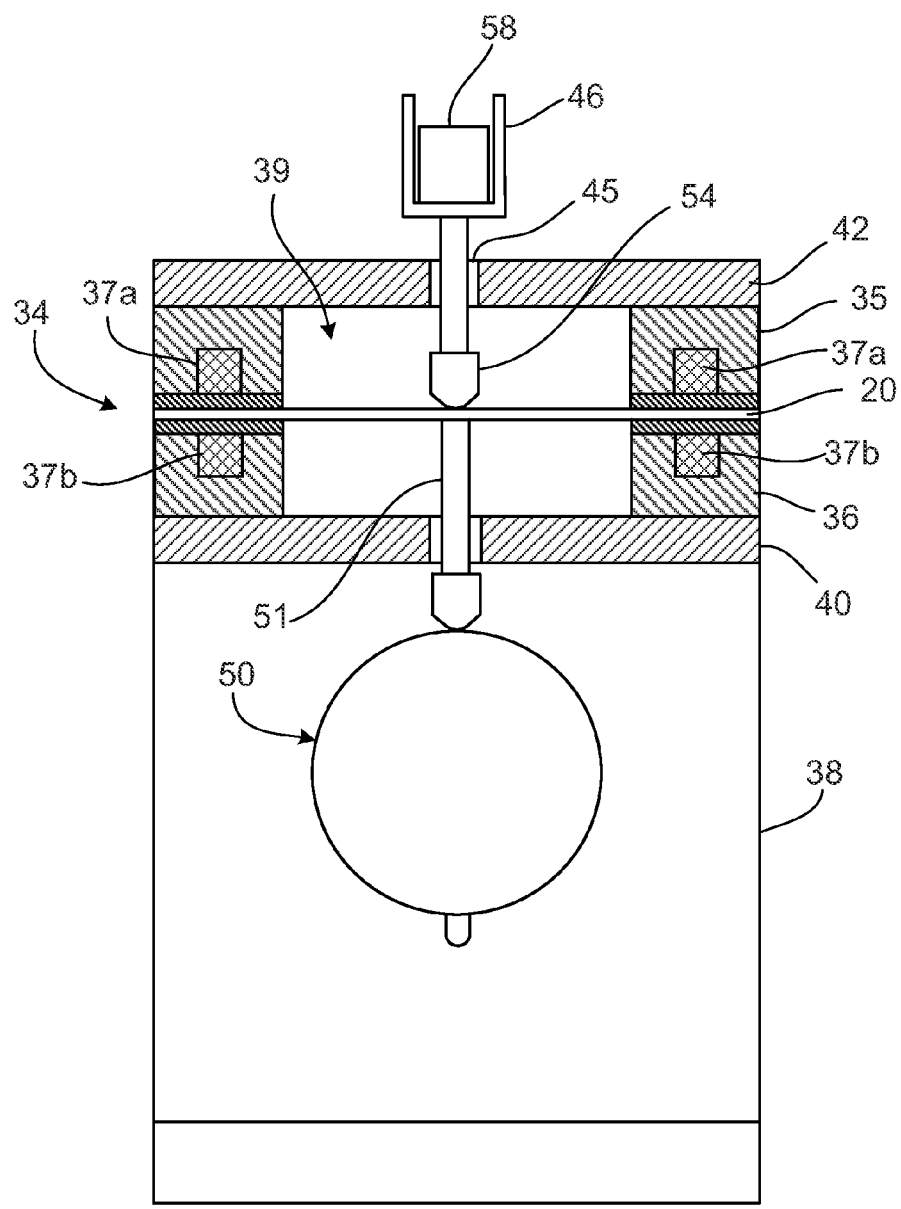
FIG. 6 is a cross-sectional view of the tissue measuring system of FIG. 1 along cross-section B-B.

Referring now to FIGS. 5 and 6, a tissue measuring system 30 includes a clamp 34, a base 38, a guide plate 42, a receptacle 46, and a deflection sensor 50. The receptacle 46 is coupled to a measuring head 54. The clamp 34 is disposed between the base 38 and the guide plate 42 such that the substantially planar biological tissue 20 is between the measuring head 54 and the deflection sensor 50.

During use, as described in further detail below, a load 58 (e.g., a brass weight) can be placed in the receptacle 46 such that a load is exerted on a portion of the biological tissue 20 supported by the clamp 34, the biological tissue 20 supported by the clamp 34 can deflect in response to the load, and the deflection sensor 50 can measure the resulting deflection of the biological tissue 20. In some embodiments, this measured deflection in response to a known load is used to determine a stress-strain relationship for the portion of biological tissue 20 supported by the clamp 34. In certain embodiments, the load exerted on the biological tissue 20 is varied (e.g., increased or decreased), the respective corresponding deflections of the biological tissue 20 measured, and a resulting stress-strain curve calculated. Based at least in part on the deflection of the biological tissue 20 in response to the applied load, the portion of the biological tissue 20 supported by the clamp 34 can be identified for use as one of the leaflets 15, 16, 17 of the replacement heart valve 10.

The clamp 34 includes a first plate 35 releasably engageable with a second plate 36 such that the substantially planar biological tissue 20 is supported between the first plate 35 and the second plate 36. As described in further detail below, the first and second plates 35 and 36 are releasably engageable by magnetic forces.

In the engaged position (shown in FIGS. 5-6), the first plate 35 and the second plate 36 define at least a portion of a test section 39 along which a portion of the substantially planar biological tissue 20 is disposed. In some embodiments, first plate 35 and the second plate 36 define the entire circumference of the test section 39. This arrangement can reduce the likelihood of inadvertent contact with the biological tissue 20 that could damage the tissue or otherwise impact load measurements. Additionally or alternatively, this circumscribed arrangement of the test section 39, loading of the biological tissue 20 is not limited to measuring deflection around the edges of the biological tissue 20. In certain embodiments, the test section 39 is partially open such that the first plate 35 and the second plate 36 define only a portion of the circumference of the test section 39. This arrangement can allow access to the test section to make any necessary adjustments and/or visual observations that may improve the quality of the load measurements. Additionally or alternatively, this partially open arrangement of the test section 39 can more closely replicate physiologic valve loading, in which the leaflet is fixed around most of its perimeter, but free along the edge that opens and closes.

The test section 39 can have an area less than the overall surface area of the secured biological tissue 20 (e.g., less than about 100 in$^2$). Additionally or alternatively, the test section 39 can have a substantially uniform cross-section extending in a direction through the clamp 34. In some embodiments, the cross-sectional area of the test section 39 in a direction extending through the clamp 34 is about equal to the surface area of a native heart leaflet. For example, in a direction extending through the clamp 34, the test section 39 can have a cross-sectional area of about 0.5 in$^2$ to about 1.0 in$^2$ (e.g., 0.58 in$^2$ or 0.67 in$^2$). In certain embodiments, the cross-sectional area of the test section 39 is substantially rectangular in a direction extending through the clamp 34. For example, the corners of the substantially rectangular shape of the test section 39 can be rounded to reduce the likelihood of high stress concentrations in the biological tissue 20.

With the first plate 35 and the second plate 36 releasably engaged with one another, a portion of the substantially planar biological tissue 20 is secured between the respective planar surfaces of the first and second plates 35, 36. In some embodiments, the ratio of the area of the releasably engageable surfaces of the first and second plates 35, 36 to the cross-sectional area of the test section 39 in a direction through the first and second plates 35, 36 is about 1.5:1 to about 4:1. This ratio can facilitate holding the biological tissue 20 in place (e.g., without trauma to and/or plastic deformation of the biological tissue 20) while a load is applied to the portion of the biological tissue 20 disposed along the test section 39.

The first and second plates 35, 36 can be formed of one or more corrosion resistant metals to allow the first and second plates 35, 36 to be exposed repeatedly to biological tissue which can be moist (e.g., from storage in a glutaraldehyde solution). For example, the first and second plates 35, 36 can be stainless steel and/or plastic (e.g., polycarbonate and/or Delrin®, available from Dupont Engineering Polymers of Wilmington, Del.). These materials can resist corrosion and resist warping or other deformation that may result in degraded performance over time. Additionally or alternatively, the first and second plates 35, 36 can be formed of one or more substantially austenitic metals which, as described in further detail below, can facilitate alignment of the first and second plates 35, 36 using one or more magnets embedded in the respective first and second plates 35, 36. In some embodiments, the first and second plates 35, 36 are formed of one or more corrosion resistant metals such that the one or more corrosion resistant metals contact the biological tissue 20.

In some embodiments, the first and second plates 35, 36 include respective first and second gaskets 35a, 36a disposed along the portion of each respective plate 35, 36 securing the biological tissue 20. The first and second gaskets 35a, 36a can be a silicone gasket material bonded or otherwise coupled to the corrosion resistant metal of the first and second plates 35, 36. The gaskets 35a, 36a can facilitate holding the biological tissue 20 in place without trauma to and/or plastic deformation of the biological tissue 20. Additionally or alternatively, the gaskets 35a, 36a can reduce the likelihood of slipping between the biological tissue 20 and the first and second plates 35, 36 as the biological tissue 20 is mounted in the clamp 34.

The first plate 35 includes at least one magnetic portion 37a, and the second plate 36 includes at least one magnetic portion 37b. The polarities of the magnetic portions 37a,b in the respective first and second plates 35, 36 are oriented to attract one another for releasable engagement of the first and second plates 35, 36. In some embodiments, the magnetic portions 37a,b are sized and arranged such that the first and second plates 35, 36 are releasably engageable with one another with a force of greater than about 0.5 lbf and less than about 5 lbf. In general, forces within this range allow for securing the biological tissue 20 in place as it is subjected to loads approximating physiological loads while not damaging or otherwise permanently deforming the biological tissue 20.

In some embodiments, forces within this range facilitate repeated detachment and attachment of the first and second plates 35, 36 along multiple, different portions of the biological tissue 20 (e.g., until a suitable portion of the biological tissue 20 is found). As compared to approaches in which biological tissue is first cut or otherwise penetrated (e.g. with needles), the magnetic attachability of the first and second plates 35,36 can improve the efficiency of selecting biological tissue meeting the mechanical criteria desired for the leaflets 15, 16, 17.

The first magnetic portions 37a and the second magnetic portions 37b are aligned with one another along respective axes extending in a direction perpendicular to the substantially planar biological tissue secured between the first and second plates 35, 36 in the engaged position. This orientation can improve the application of force onto the biological tissue 20 such that a substantial gripping force can hold the biological tissue 20 in place as the measuring head 54 applies a load to the biological tissue 20. In some embodiments, with the plates 35, 36 in the engaged position, the first magnetic portions 37a of the first plate 35 and the second magnetic portions 37b of the second plate 36 each define axes that extend through (e.g., bisect) the test section 39.

In some embodiments, the first magnetic portions 37a and the second magnetic portions 37b are respective magnets embedded in the respective first and second plates 35, 36. For example, the first and second magnetic portions 37a,b can be rare earth magnets (e.g., samarium-cobalt) which can provide a high level of corrosion resistance with high magnetic pull. Additionally or alternatively, the first and second magnetic portions 37a,b can be aluminum-nickel-cobalt magnets to provide medium magnetic pull and/or ceramic magnets to provide low/medium magnetic pull. In certain embodiments, the magnetic portions 37a,b are embedded in the respective first and second plates 35, 36 using a potting material. Examples of suitable potting materials include one or more of epoxy and/or polyurethane potting materials. In general, the potting material does not alter the magnetic fields associated with the first and second magnetic portions 37a,b, but protects the first and second magnetic portions 37a,b from corrosion that can otherwise result from exposure to the biological tissue 20.

The base 38 supports the clamp 34, the receptacle 46, and the deflection sensor 50 in place to facilitate the application of a load to the biological tissue 20 disposed along the test section 39 of the clamp 34. In some embodiments, the base 38 is made of a corrosion resistant metal (e.g., stainless steel) to reduce the likelihood that the base 38 will corrode over time through repeated contact with biological tissue and chemicals used to treat and/or store the biological tissue (e.g., glutaraldehyde solutions). In some embodiments, the base includes a cantilevered portion 40 upon which the clamp 34 is at least partially supported and below which the deflection sensor 50 is positioned.

The cantilevered portion 40 can protect the deflection sensor 50 as the clamp 34 and the receptacle 46 are mounted above the cantilevered portion 40. In certain embodiments, the cantilevered portion 40 has a footprint substantially similar to the footprint of the clamp 34. This can facilitate alignment of the clamp 34 on the cantilevered portion 40 (e.g., alignment can be achieved by aligning one or more edges of the clamp 34 to one or more edges of the cantilevered portion 40). Additionally or alternatively, the clamp 34 can be aligned and held in a substantially fixed position relative to the cantilevered portion 40 by one or more structural features (not shown in FIGS. 5 and 6) such as, for example, one or more pins extending from the cantilevered portion 40 and into the second plate 36.

The guide plate 42 is supported on the first plate 35 and defines an orifice 45 through which the measuring head 54 is coupled to the receptacle 46. The orifice 45 is sized such that the measuring head 54 can move freely relative to the test section 39. This can improve accuracy of measurement by, for example, facilitating transmission of the entire load held in the receptacle 46 to the biological tissue 20. At least a portion of the guide plate 42 can be made of a corrosion resistant metal such as, for example, stainless steel. In some embodiments, at least a portion of the guide plate 42 can be made of an optically transparent material (e.g., poly(methyl methacrylate)) to allow, for example, visual observation of the load applied to the biological tissue 20.

The guide plate 42 is aligned relative to the clamp 34 by one or more pins 44 extending through the guide plate 42 and into the first plate 35. It should be appreciated that the point of application of load on the biological tissue 20 disposed in the test section 39 is determined by the relative positioning of the guide plate 42 to the clamp 34 and the relative positioning of the orifice 45 on the guide plate 42. For example, the orifice 45 can be substantially centered on the guide plate 42 and the guide plate 42 can have approximately the same dimensions as the first and second plates 35 and 36 such that load is applied at a substantially central point of the biological tissue 20 disposed along the test section 39. In some embodiments, guide plate 42 defines more than one orifice 45 such that the measuring head 54 can apply load at other points (e.g., simultaneously or individually) of the biological tissue 20 disposed along the test section 39. In certain embodiments, the orifice 45 is sized such that the measuring head 54 is positionable at any point along the cross-sectional area of the test section 39 to apply a load at any point along the biological tissue 20 disposed along the test section 39.

The measuring head 54 is coupled to the receptacle 46 such that the load 58 placed in the receptacle is transmitted to the measuring head 54 and, ultimately, to the portion of the biological tissue 20 disposed along the test section 39. The measuring head 54 includes a substantially rounded surface (e.g., a substantially arcuate surface) movable into contact with the biological tissue 20 to apply a point load perpendicular to the biological tissue 20 disposed along the test section. The substantially rounded surface of the measuring head 54 can facilitate atraumatic application of the point load to the biological tissue 20 such that the stress-strain test carried out using the tissue measuring system 30 is non-destructive to the biological tissue 20. In use, the measuring head 54 contacts the biological tissue 20. Thus, in some embodiments, the measuring head 54 includes one or more corrosion resistant materials such as, for example, stainless steel.

In certain embodiments, the measuring head 54 has a substantially circular cross-sectional area such that the substantially rounded surface of the measuring head 54 applies a point load to the biological tissue 20 disposed along the test section 39. In some embodiments, the substantially rounded surface of the measuring head 54 is substantially elongate to apply an axial load to the biological tissue 20 disposed along the test section 39. For example, the measuring head 54 can be rotatable with respect to the biological tissue 20 disposed along the test section 20 to apply an axial load along any of various axes parallel to the biological tissue 20 disposed along the test section 20.

In some embodiments, a maximum cross-sectional area of the measuring head 54 is smaller than the cross-sectional area of the orifice 45 defined by the guide plate 42 to facilitate assembly of the tissue measuring system 30 and/or to facilitate application of load to different portions of the biological tissue 20. In certain embodiments, a maximum cross-sectional area of measuring head 54 is larger than the cross-sectional area of the orifice 45 such that the guide plate 42 may limit movement of the measuring head 54. This can, for example, reduce the likelihood that the measuring head 54 would become separated from the guide plate 42 during assembly and disassembly of the tissue measuring system 30.

The deflection sensor 50 is mounted substantially opposite the measuring head 54 such that the measuring head 54 is disposed on a first side of the biological tissue 20 disposed along the test section 39 and the deflection sensor 50 is disposed on a second, opposite side of the biological tissue. It should be appreciated that the force exerted by the measuring head 54 on the biological tissue 20 causes the biological tissue to deform (e.g., elastically deform). The deformation of the biological tissue 20 is measured by the deflection sensor 50.

In some embodiments, the deflection sensor 50 is an electromechanical displacement indicator, such as a Digimatic Indicator having model number ID-C1012CE, available from Mitutoyo, U.S.A. of Aurora, Ill. In these embodiments, the deflection sensor 50 includes a spring-loaded spindle 51 biased to contact the biological tissue 20. In response to the perpendicular load exerted on the biological tissue 20 by the measuring head 54, the biological tissue 20 deforms and the spindle 51 moves in proportion to the elastic deformation of the biological tissue.

The deflection sensor 50 can be in electrical communication with a computer 60 such that a signal proportional to the measured deflection is transmitted from the deflection sensor 50 to the computer 60. The signal from the deflection sensor 50 can be stored on the computer 60. Additionally or alternatively, the stored signal can be associated with a particular portion of the biological tissue 20 (e.g., to create a stress-strain map of the biological tissue). In certain embodiments, the computer 60 can convert the measured deflection into a strain value.

Figure 7:
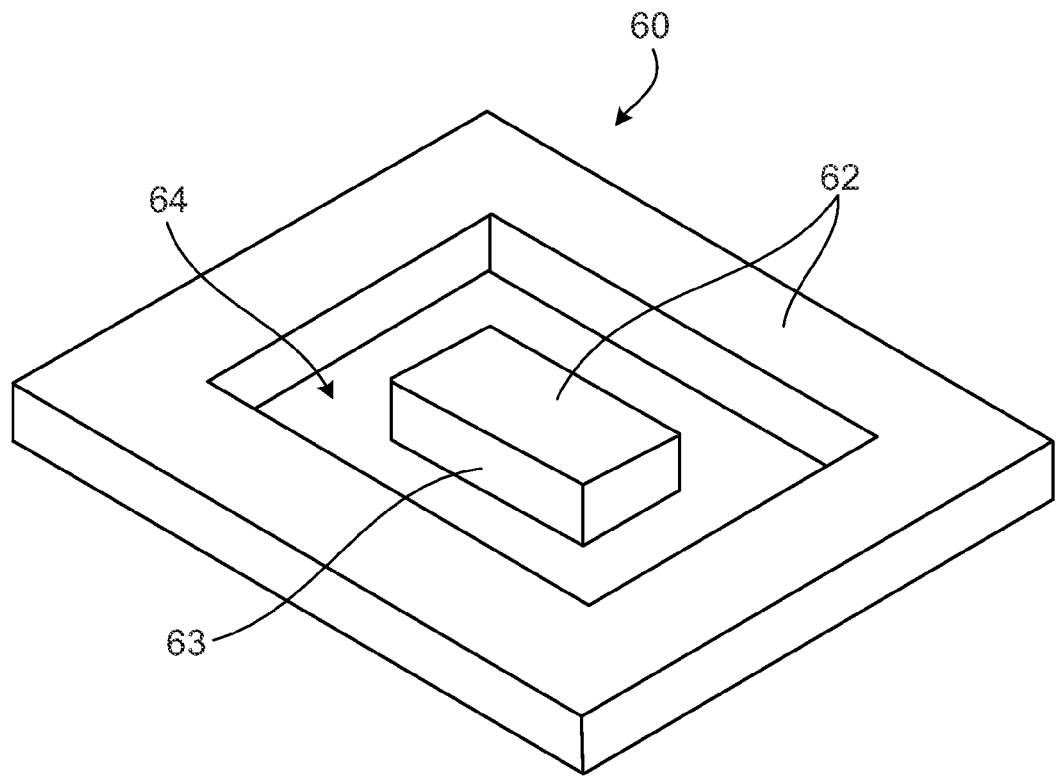
FIG. 7 is a perspective view of a frame.
Figure 8:
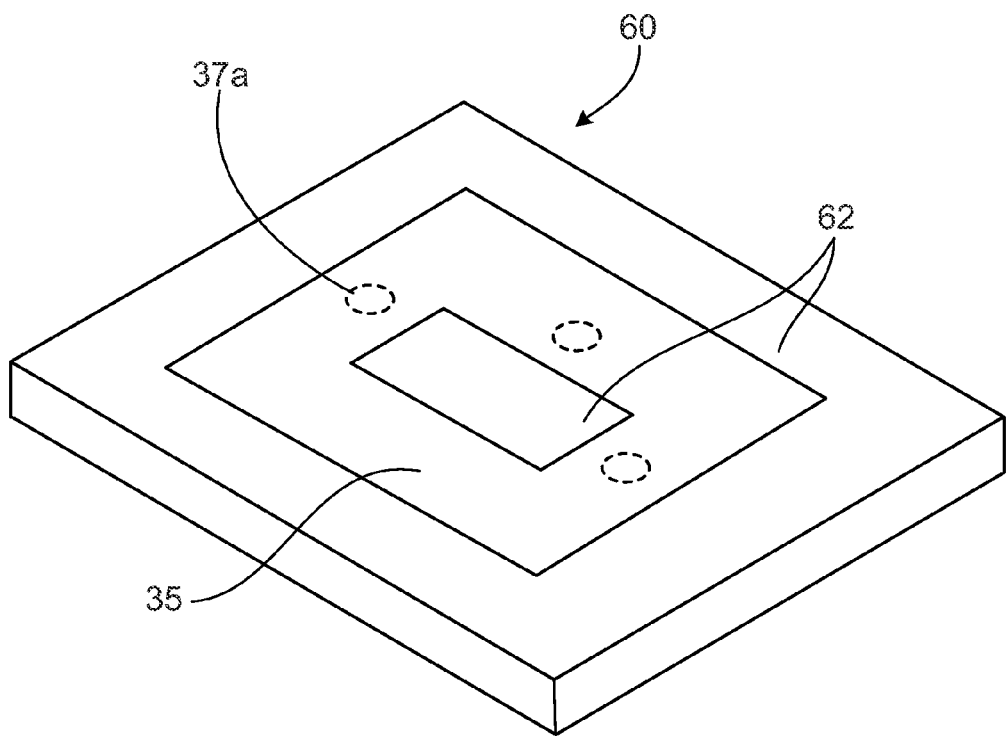
FIG. 8 is a perspective view of a plate disposed in the frame of FIG. 7.
Figure 9:
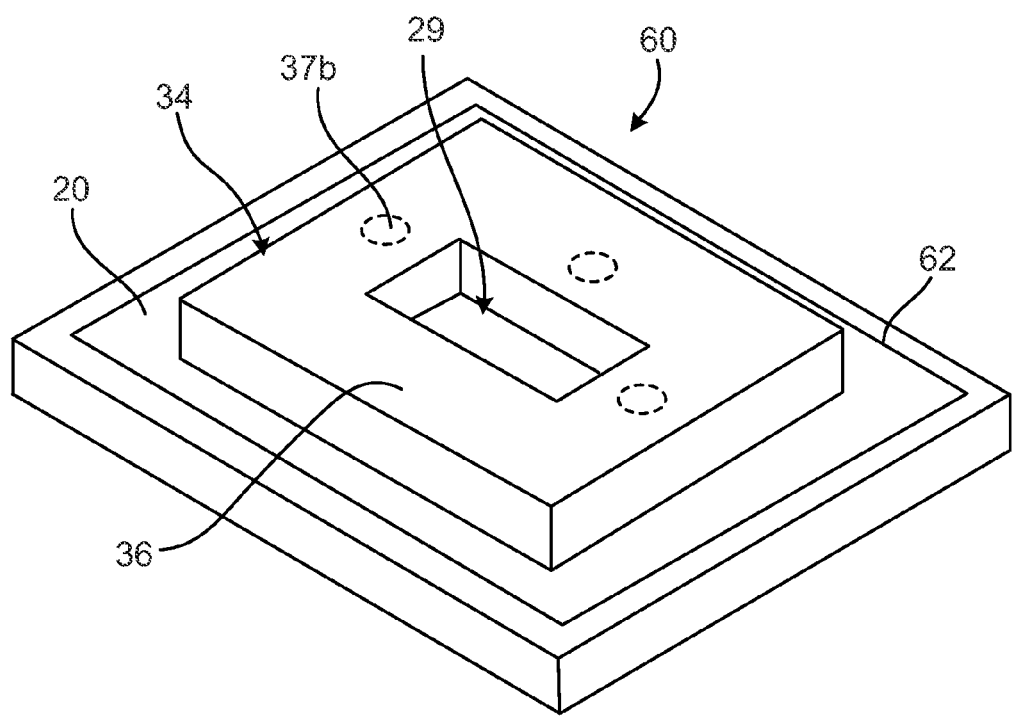
FIG. 9 is a perspective view of a clamp in the frame of FIG. 7.

Referring now to FIGS. 7-9, a frame 60 facilitates alignment of the biological tissue 20 with the test section 39 defined by the first and second plates 35, 36. Such alignment can facilitate analysis of portions of interest of the biological tissue 20. For example, if it is determined that a portion of the biological tissue 20 has a thickness that may be suitable for use as a leaflet 15, 16, 17, the biological tissue 20 can be positioned such that the portion of interest is disposed along the test section 39.

The frame 60 has a substantially planar surface 62 and defines a recess 64 around a central portion 63. The frame 60 can be made of one or more corrosion resistant materials and/or substantially non-magnetic materials. For example, the frame 60 can be made of stainless steel. In some embodiments, outer dimensions of the frame 60 are larger than the outer dimensions of the first and second plates 35, 36. In certain embodiments, the outer dimensions of the frame 60 are larger than the outer dimensions of the biological tissue 20 being analyzed. For example, the outer dimensions of the substantially planar surface 62 of the frame 60 can be greater than about 8 inches and greater than about 10 inches.

The first plate 35 is positionable into the recess 64 such that the first plate 35 and the substantially planar surface 62 of the frame 60 form a substantially continuous planar surface. The biological tissue 20 can be placed on the substantially continuous planar surface formed by the first plate 35 and the substantially planar surface 62 of the frame 60. The biological tissue 20 is placed such that it is substantially flat (e.g., free of folds or bumps). In instances in which a particular portion of the biological tissue 20 is to be analyzed, that portion of the biological tissue 20 is positioned above the central portion 63 of the frame 60. As described in further detail below, such positioning of the biological tissue 20 results in the portion of interest being disposed along the test section 29 when the first and second plates 35, 26 are releasably engaged with one another.

The second plate 36 is positionable over the first plate 35 and the biological tissue 20 such that magnetic portions 37b of the second plate 36 attract corresponding magnetic portions 37a of the first plate 35 to form the clamp 34. With the first and second plates 35, 36 releasably engaged based at least in part on the magnetic attraction between the respective first and second magnetic portions 37a,b, the biological tissue 20 is secured between the first and second plates 35, 36 and the first and second plates 35, 36 define the test section 29.

The clamp 34 and the secured biological tissue 20 can be removed from the frame 60 for placement into the tissue measuring system 30. In some embodiments, the magnetic attraction forces between the first and second magnetic portions 37a,b of the respective first and second plates 35, 36 are sufficient to allow the clamp 34 and the secured biological tissue 20 to be removed from the frame 60 by grasping the second plate 36. In certain embodiments, the clamp 34 and the secured biological tissue 20 can be removed from the frame 60 by turning the frame to allow the clamp 34 to move out of the frame 60 under the force of gravity.

While the foregoing discussion describes the placement of the first plate 35 into the frame 60, it should be appreciated that the second plate 36 can be placed into the frame 60 and the first plate 35 placed over the second plate 36 and the biological tissue 20.

Figure 10:
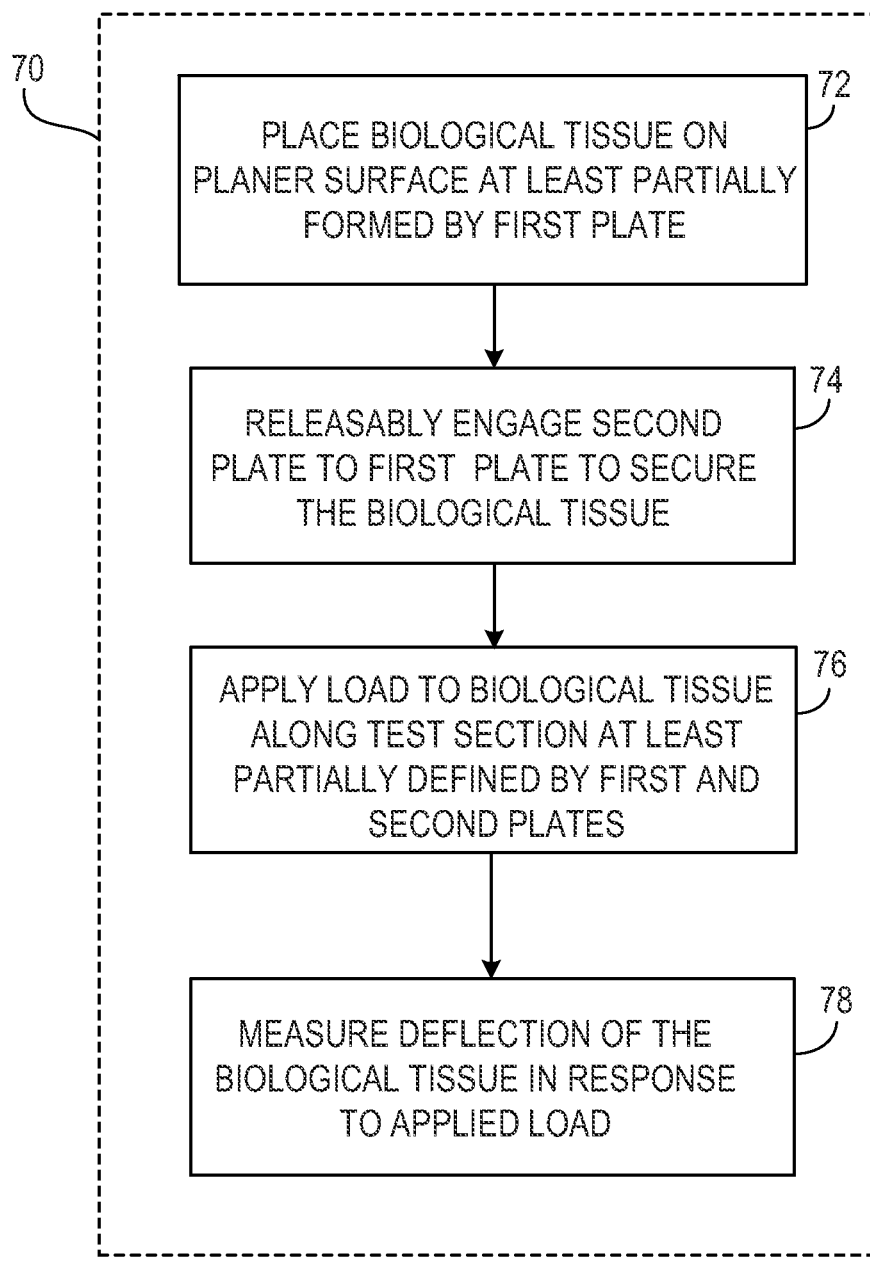
FIG. 10 is a schematic of a method of selecting tissue.

Referring now FIG. 10, a method 70 of using a tissue measuring system (e.g., tissue measuring system 30) to measure a biological tissue includes placing 72 a substantially planar biological tissue on a planar surface at least partially formed by a first plate, releasably engaging 74 a second plate to the first plate such that the substantially planar biological tissue is secured between the first and second plates, applying 76 a load to the portion of the substantially planar biological tissue disposed along a test section at least partially defined by the first and second plates, and measuring 78 deflection of the biological tissue in response to the applied load.

Placing 72 the substantially planar biological tissue on a planar surface at least partially formed by the first plate can include placing the biological tissue 20 on the first plate 35 and frame 60, as described above with respect to FIGS. 7-9, such that the first plate 35 and the frame 60 form the planar surface. In some embodiments, the planar surface can be a sterilized surface.

Releasably engaging 74 the second plate to the first plate includes releasably engaging the second plate to the first plate such that the substantially planar biological tissue is secured between the first and second plates. The first and second plates define at least a portion of a test section along which a portion of the secured substantially planar biological tissue is disposed. In some embodiments, releasably engaging 74 the second plate to the first plate includes releasably engaging the second plate 36 to the first plate 35, as described above with respect to FIGS. 7-9. For example, releasably engaging 74 the second plate to the first plate can include placing the second plate on the substantially planar biological tissue disposed on the planar surface at least partially formed by the first plate. Additionally or alternatively, releasably engaging 74 the second plate to the first plate can include aligning respective magnetic portions of the first and second plates.

Applying 76 the load to the portion of the substantially planar biological tissue disposed along the test section at least partially defined by the first and second plates can include applying a static and/or a dynamic load along one or more portions of the planar biological tissue disposed along the test section. For example, applying 76 the load can include placing the load 58 into the receptacle 46 in communication with the measuring head 54 movable perpendicular to and into contact with the substantially planar biological tissue 20 disposed along the test section 29, as described above with respect to FIGS. 5-6. Such static loading can facilitate reliable and repeatable testing of the biological tissue through test procedures that can be implemented in production settings. Additionally or alternatively, applying 76 the load can include applying a dynamic load (e.g., progressively increasing load, progressive decreasing load, pulsating load) to the substantially planar biological tissue to measure the dynamic response of the biological tissue. Such dynamic loading can facilitate selection of biological tissue that will substantially match the response of healthy native leaflets in response to pulsatile flow, such as the flow through a normal, mammalian aortic heart valve.

To achieve a given stress level in the biological tissue, it should be appreciated that the load applied to the biological tissue can vary depending on the size and shape of the test section. In some embodiments, applying 76 the load to the portion of the substantially planar biological tissue disposed along the test section includes applying a load that replicates the average stress of a normal native leaflet. For example, finite element analysis (FEA) can be used to model the stress on a normal native leaflet under physiological conditions. The average stress can be determined from this analysis and the load applied to the biological tissue can replicate the average of this stress.

Measuring 78 deflection of the biological tissue in response to the applied 76 load can include measuring the deflection of the biological tissue 20 by the deflection sensor 50, as described above with respect to FIGS. 5-6. Additionally or alternatively, measuring the deflection of the biological tissue in response to the applied load 76 can include one or more optical detectors (e.g. a laser), which can measure deflection of the biological tissue without contacting the biological tissue and, thus, reduce the potential for damaging and/or contaminating the tissue.

In some embodiments, the measured 78 deflection is compared to a selection range. For example, the measured 78 deflection can be compared to a minimum acceptable value of deflection and a maximum acceptable value of deflection. Additionally or alternatively, the measured 78 deflection can be an average of a series of deflections and the average deflection can be compared to a minimum acceptable value of deflection and a maximum acceptable value of deflection.

In some embodiments, the portion of the biological tissue disposed along the test section is within an acceptable selection range and a leaflet can be cut from the portion of the biological tissue found to be within the selection range. For example, the leaflet shape can be cut by introduction of a blade or other cutting tool into the test section defined by the first and second plates. Additionally or alternatively, the leaflet shape can be cut using a laser directed at the biological tissue disposed along the test section defined by the first and second plate. In some embodiments, the portion of the biological tissue having acceptable deflection characteristics is identified (e.g., by non-destructive marking) for a cutting procedure performed with the biological tissue removed from between the first and second plates.

In certain embodiments, the portion of the biological tissue disposed along the test section is outside of an acceptable selection range and the first and second plates are repositioned along the biological tissue. For example, the first and second plates can be detached from one another and moved relative to the substantially planar biological tissue such that a second, different portion of the substantially planar biological tissue is disposed along the test section. In embodiments in which the first and second plates are releasably engageable with one another through magnetic force, for example, the first and second plates can be repositioned without damage to the biological tissue. As compared to methods that require cutting or otherwise altering the structure of biological tissue, such repositioning is non-destructive and can facilitate rapid and efficient characterization of biological tissue used to form leaflets of replacement heart valves. Additionally or alternatively, as compared to methods that require cutting or otherwise altering the structure of biological tissue, such repositioning can facilitate tissue leaflet matching to within narrower tolerances, resulting in improved hemodynamic performance of the leaflets used in replacement heart valves.

While certain embodiments have been described, other embodiments are possible.

For example, while the biological tissue disposed along the test section has been described as being measured for deflection under an applied load, other embodiments are additionally or alternatively possible. In some embodiments, the thickness at one or more points along the tissue disposed along the test section is determined. For example, the thickness of the tissue can be measured using a snap gauge before and/or after deflection of the tissue is measured under load.

Figure 11:
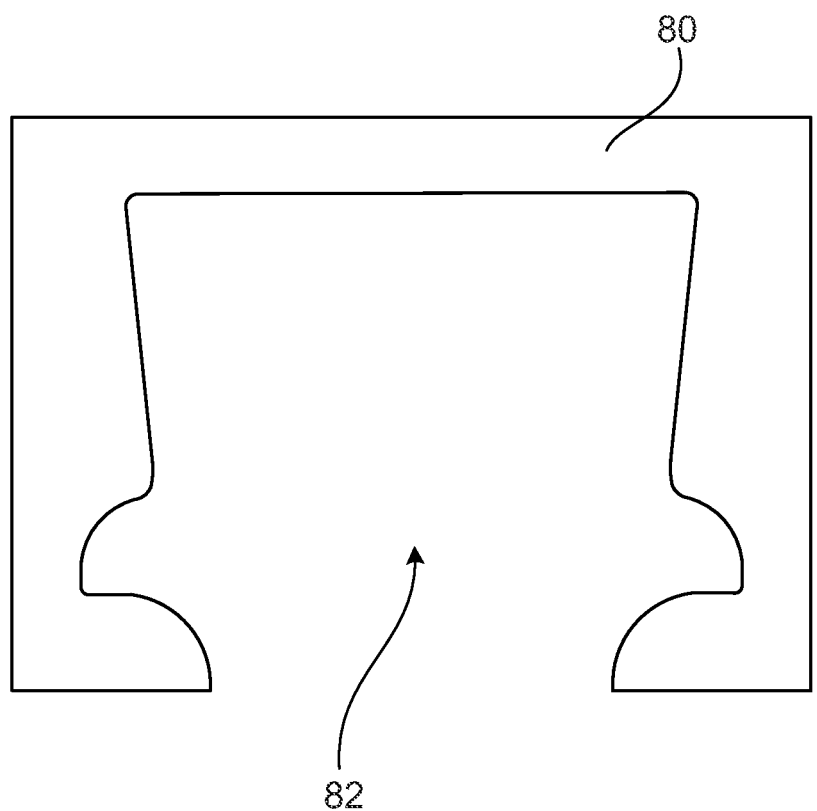
FIG. 11 is a top view of a plate of a tissue measuring system.

As another example, while the test section has been described as being substantially rectangular, other embodiments are additionally or alternatively possible. In some embodiments, the cross-sectional area of the test section is substantially identical to the shape of a leaflet used in the replacement heart valve. For example, referring to FIG. 11, a first plate 80 defines a recess 82 having a circumference approximately matching the shape of the leaflets 15, 16, 17 prior to formation into the leaflet assembly 14 and attachment to the replacement heart valve 10.

Figure 12A:
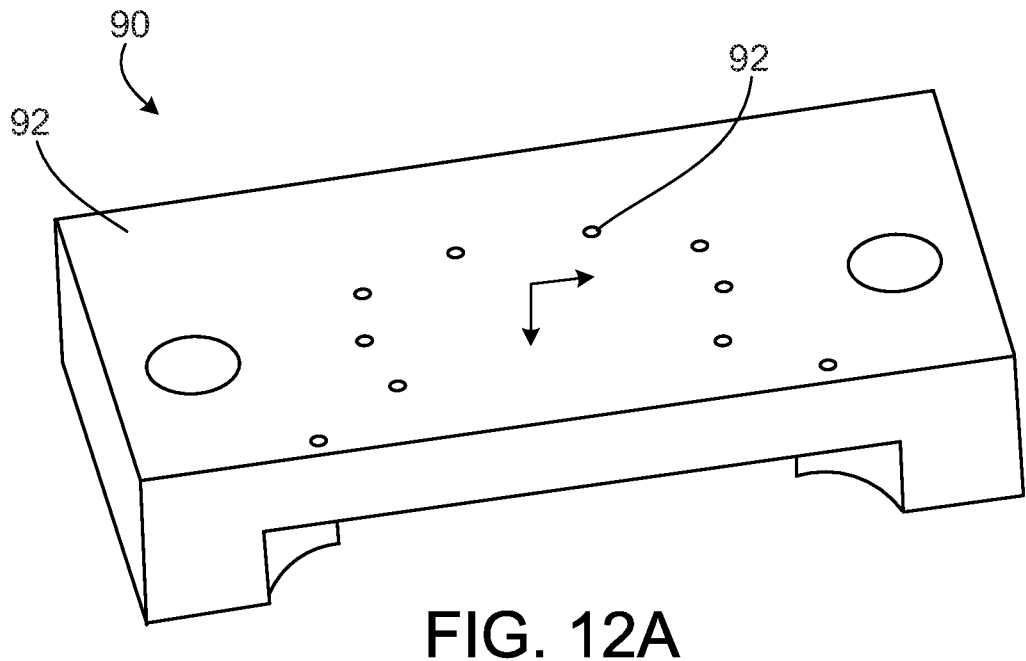
FIG. 12A is a perspective view of a positioning plate.

As yet another example, while the first and second plates have been described as releasably engageable through magnetic forces, other embodiments are additionally or alternatively possible. In some embodiments, pins hold a biological tissue in place along a test section defined by a first and a second plate. For example, referring to FIGS. 12A-B, a positioning plate 90 has a planar surface 92 and defines a plurality of holes 92 extending from the planar surface 92 into the positioning plate 90. The holes 92 are spaces apart and define the boundaries of a test section. A clamp plate 100 has a recessed portion 102 defining a plurality of holes 104 extending from the recessed portion 102 into the clamp plate 100 and defining a portion of a test section.

Figure 12B:
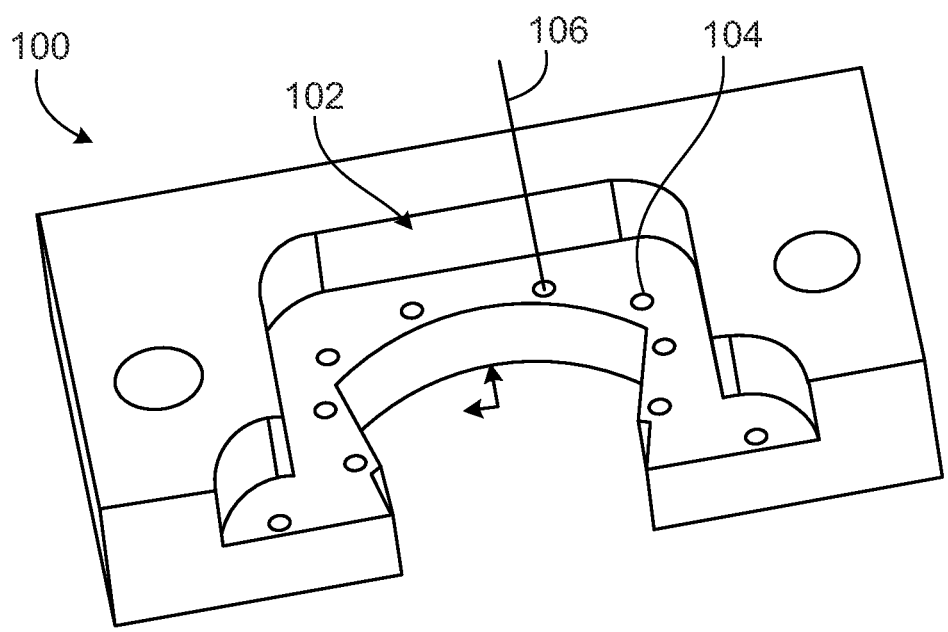
FIG. 12B is a perspective view of a plate of a tissue measuring system.

In use, a substantially planar sheet of biological tissue (e.g., biological tissue 20) is laid flat on the planar surface 92 so that there is no extra tissue or slack along the portion of the planar surface 92 defining the test section. The clamp plate 100 includes needles 106 (for purposes of illustration, a single needle 106 is shown in FIG. 12B) press fit into each of plurality of holes 104. The clamp plate 100 is pressed onto the positioning plate 90 such that the needles extend through the biological tissue and into corresponding holes 92 of the positioning plate 90. The positioning plate 90 is then removed, leaving the biological tissue mounted on the clamp plate 100 by the needles. Another plate, substantially identical to the clamp plate 100, can then be positioned on the clamp plate 100 such that the needles hold the plates in a fixed position relative to each other and hold the biological tissue in place along a test section defined by the mating clamp plates 100. If the biological tissue disposed between the clamp plates 100 exhibits desired deflection characteristics, the portion of the biological tissue that has been penetrated by the needles can be cut away and the remainder of the biological tissue can be used to form at least a portion of a valve leaflet.

Figure 13:
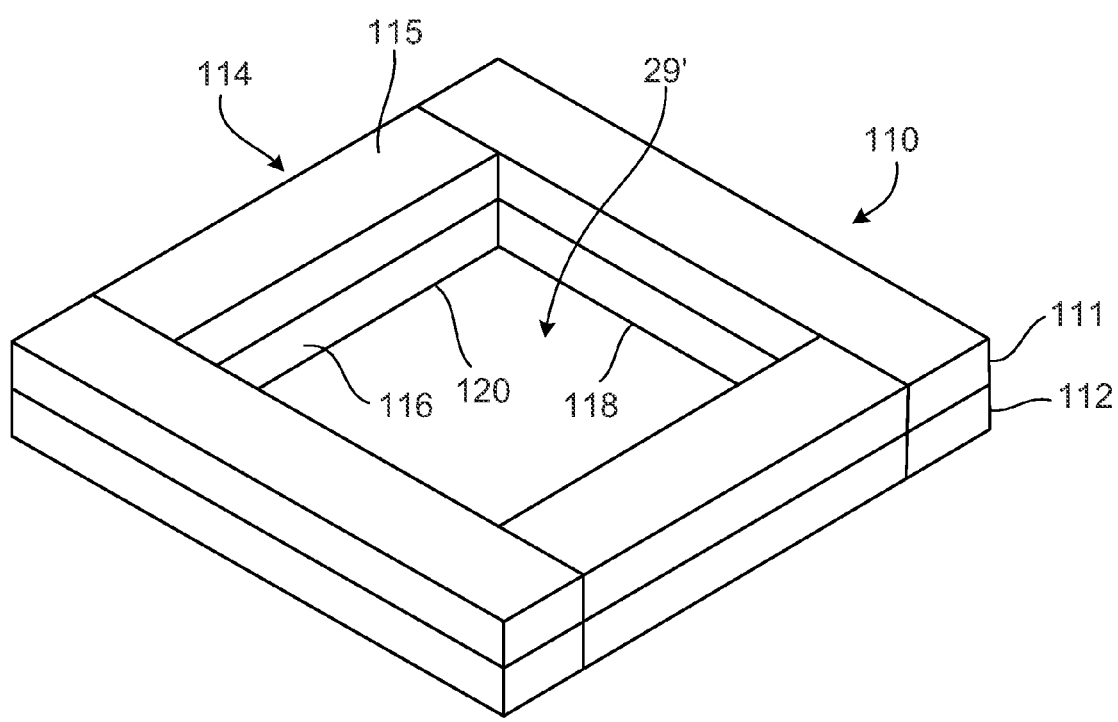
FIG. 13 is a perspective view of a first and a second clamp of a tissue measuring system.

As still another example, while the clamp has been described as being a first plate and a second plate that define a test section, other embodiments are additionally or alternatively possible. For example, referring to FIG. 13, a tissue measuring system can include a first clamp 110 and a second clamp 114, each defining at least a portion of a test section 29'. For clarity of description, only the first clamp 110 and the second clamp 114 are described in detail. However, it should be appreciated that the first clamp 110 and the second clamp 114 can each have substantially identical counterparts such that the test section 29' is enclosed as shown in FIG. 13.

The first clamp 110 includes a first plate 111 and a second plate 112. The first plate 111 and the second plate 112 are releasably engageable with one another to secure therebetween a substantially planar biological tissue (e.g., biological tissue 20 in FIG. 4). In this releasably engaged position, the first and second plates 111, 112 define at least a first portion 118 of the test section 29' along which a portion of the secured biological tissue is disposed.

The second clamp 114 includes a third plate 115 and a fourth plate 116. The third plate 115 and the fourth plate 116 are releasably engageable with one another (e.g., through the force of magnets) to secure therebetween a substantially planar biological tissue (e.g., biological tissue 20 in FIG. 4). In this releasably engaged position, the third and fourth plates 115, 116 define at least a second portion 120 of the test section 29' along which a portion of the secured biological tissue is disposed.

In some embodiments, the first portion 118 of the test section 29' defined by the engaged first and second plates 111 and 112 is substantially coplanar and perpendicular to the second portion 120 of the test section defined by the engaged third 115 and fourth 116 plates. This coplanar and perpendicular orientation can facilitate securing the biological tissue by the first and/or second clamps 110, 114. Additionally or alternatively, this coplanar and perpendicular orientation can facilitate precise application of load on the biological tissue along multiple, different axes.

In use, a measuring head (e.g., measuring head 54 in FIG. 6) is moved toward the test section 29' into contact with biological tissue disposed along the test section 29'. A deflection sensor (e.g., deflection sensor 50 in FIG. 6) is responsive to movement of the biological tissue contacted by the measuring head. As described in further detail below, the measuring head can be used to apply forces along one or more axes such that the resulting stress response can be measured along one or more axes (e.g., two perpendicular axes). In some embodiments, biological tissue can be selected based on matching stress criteria along the one or more axes.

In certain embodiments, the first and second clamps 110, 114 are separately removable from the substantially planar biological tissue disposed along the test section 29'. For example, the first clamp 110 can be removed from the biological tissue, while the biological tissue remains secured by the second clamp 114. Additionally or alternatively, the second clamp 114 can be removed from the biological tissue, while the biological tissue remains secured by the first clamp 110. The separate removability of the first and second clamps 110, 114 can facilitate application of force along one or more axes of the biological tissue. For example, with the biological tissue secured by the first clamp 110, the deflection response of the biological tissue can be measured in response to an axial load applied substantially parallel to the first portion 118 of the test section 29' defined by the first clamp 110. Similarly, with the biological tissue secured by the second clamp 114, the deflection response of the biological tissue can be measured in response to an axial load applied substantially parallel to the second portion 120 of the test section 29' defined by the second clamp 114. In some embodiments, forces can additionally or alternatively be applied along one or more axes intersecting (e.g., perpendicular to) the respective first and second sections 118, 120 of the test section 29'.

A number of embodiments of the invention have been described. Nevertheless, it will be understood that various modifications may be made without departing from the spirit and scope of the invention. For example, the measuring head and the deflection sensor have been described as being on opposite sides of the biological tissue, the measuring head and the deflection sensor can be on the same side of the biological tissue. Accordingly, other embodiments are within the scope of the following claims.

What is claimed is:

1. A tissue measurement system comprising:
a clamp comprising a first plate and a second plate, the first and second plates releasably engageable with one another to secure therebetween a substantially planar biological tissue and the first and second plates, in an engaged position, defining at least a portion of a test section along which a portion of the secured substantially planar biological tissue is disposed;
a measuring head movable relative to the test section and into contact with the portion of the substantially planar biological tissue disposed along the test section;
a deflection sensor responsive to movement of the biological tissue contacted by the measuring head; and
a receptacle coupled to the measuring head such that a load supported in the receptacle is transmittable to the biological tissue disposed along the test section.

2. The tissue measurement system of claim 1, wherein the measuring head comprises a substantially rounded surface movable into contact with the biological tissue to apply a point load perpendicular to the biological tissue disposed along the test section.

3. The tissue measurement system of claim 1, wherein the measuring head comprises a substantially rounded elongate surface movable into contact with the biological tissue to apply an axial load perpendicular to the biological tissue disposed along the test section.

4. A tissue measurement system comprising:
a clamp comprising a first plate and a second plate, the first and second plates releasably engageable with one another to secure therebetween a substantially planar biological tissue and the first and second plates, in an engaged position, defining at least a portion of a test section along which a portion of the secured substantially planar biological tissue is disposed, wherein the first plate comprises a first magnetic portion, the second plate comprises a second magnetic portion, and polarities of the first and second magnetic portions are oriented to attract one another for releasable engagement of the first and second plates of the clamp;
a measuring head movable relative to the test section and into contact with the portion of the substantially planar biological tissue disposed along the test section; and
a deflection sensor responsive to movement of the biological tissue contacted by the measuring head.

5. The tissue measurement system of claim 4, wherein, with the first and second plates in the engaged position, the first magnetic portion and the second magnetic portion are aligned along an axis extending in a direction perpendicular to the substantially planar biological tissue secured between the first and second plates in the engaged position.

6. The tissue measurement system of claim 4, wherein the first magnetic portion comprises a first magnet embedded in the first plate and the second magnetic portion comprises a second magnet embedded in the second plate.

7. The tissue measurement system of claim 1, further comprising a plurality of needles, wherein the first plate comprises a first plurality of orifices and the second plate comprises a second plurality of orifices, each of the plurality of needles positionable in one of the first plurality of orifices and one of the second plurality of orifices to releasably engage the first plate to the second plate.

8. The tissue measurement system of claim 1, wherein the first and second plates are releasably engageable with one another with a force of greater than about 0.5 lbf and less than about 5 lbf.

9. The tissue measurement system of claim 1, wherein the measuring head is movable into a contact with a first surface of the biological tissue and the deflection sensor is responsive to movement of a second surface of the biological tissue opposite the first side of the biological tissue.

10. A tissue measurement system comprising:
a clamp comprising a first plate and a second plate, the first and second plates releasably engageable with one another to secure therebetween a substantially planar biological tissue and the first and second plates, in an engaged position, defining at least a portion of a test section along which a portion of the secured substantially planar biological tissue is disposed;
a measuring head movable relative to the test section and into contact with the portion of the substantially planar biological tissue disposed along the test section, wherein the measuring head is movable into a contact with a first surface of the biological tissue and the deflection sensor is responsive to movement of a second surface of the biological tissue opposite the first side of the biological tissue; and
a deflection sensor responsive to movement of the biological tissue contacted by the measuring head, wherein the deflection sensor comprises a spring-loaded spindle movable in a first direction to contact the second side of the biological tissue and movable in a second, opposite direction in response to movement of the second side of the biological tissue.

11. The tissue measurement system of claim 1, wherein the test section has an area less than a surface area of the secured substantially planar biological tissue.

12. The tissue measurement system of claim 1, wherein each of the first and second plates has a respective substantially planar surface and the first section and the second plates are releasably engageable with one another to secure the substantially planar biological tissue between the respective substantially planar surfaces.

13. The tissue measurement system of claim 1, wherein the test section extends through the first and second plates and is entirely defined by the first and second plates in the engaged position.

14. The tissue measurement system of claim 1, wherein each of the first and second plates comprises a respective gasket and the first and second plates are releasably engageable with one another to secure the substantially planar biological tissue between the respective gaskets.

15. The tissue measurement system of claim 1, wherein the measuring head is movable in a direction perpendicular to a cross-sectional area of the test section.

16. The tissue measurement system of claim 1, wherein the deflection sensor is in electrical communication with a computer, and the deflection sensor is configured to send to the computer a signal representative of displacement.

17. The tissue measurement system of claim 1, wherein the first and second plates are made of one or more of stainless steel and plastic.

18. A tissue measurement system comprising:
a first clamp comprising a first plate and a second plate, the first and second plates releasably engageable with one another to secure therebetween a substantially planar biological tissue, and the first and second plates, in an engaged position, defining at least a first portion of a test section along which a portion of the secured substantially planar biological tissue is disposed;
a second clamp comprising a third plate and a fourth plate, the third and fourth plates releasably engageable with one another to secure therebetween the substantially planar biological tissue, and the third and fourth plates, in an engaged position, defining at least a second portion of a test section along which a portion of the secured substantially planar biological tissue is disposed;
a measuring head movable toward the test section and into contact with the portion of the substantially planar biological tissue disposed along the test section;
a deflection sensor responsive to movement of the biological tissue contacted by the measuring head; and
a receptacle coupled to the measuring head such that a load supported in the receptacle is transmittable to the biological tissue disposed along the test section.

* * * * *